United States Patent
Carnali et al.

(10) Patent No.: US 8,652,450 B2
(45) Date of Patent: *Feb. 18, 2014

(54) SOAP-BASED LIQUID WASH FORMULATIONS WITH ENHANCED DEPOSITION OF CONDITIONING AND/OR SKIN APPEARANCE ENHANCING AGENTS

(75) Inventors: Joseph Oreste Carnali, Newtown, CT (US); Pravin Shah, Rutherford, NJ (US); Qiang Qiu, Trumbull, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 262 days.

This patent is subject to a terminal disclaimer.

(21) Appl. No.: 12/255,349

(22) Filed: Oct. 21, 2008

(65) Prior Publication Data

US 2010/0098646 A1    Apr. 22, 2010

(51) Int. Cl.
*A61K 8/19* (2006.01)
*A61K 8/29* (2006.01)
*A61K 47/44* (2006.01)

(52) U.S. Cl.
USPC .......................................................... 424/63

(58) Field of Classification Search
None
See application file for complete search history.

(56) References Cited

U.S. PATENT DOCUMENTS

| 5,308,526 | A | 5/1994 | Dias et al. |
| 5,312,559 | A | 5/1994 | Kacher et al. |
| 6,987,085 | B2 | 1/2006 | Seki |
| 2003/0078172 | A1 | 4/2003 | Guiramand et al. |
| 2004/0048758 | A1* | 3/2004 | Zhang et al. .................. 510/130 |
| 2004/0223929 | A1 | 11/2004 | Clapp et al. |
| 2004/0234565 | A1 | 11/2004 | Stella et al. |
| 2005/0100570 | A1 | 5/2005 | Wei et al. |
| 2006/0239953 | A1 | 10/2006 | Clapp et al. |
| 2006/0246149 | A1 | 11/2006 | Buchholz et al. |
| 2007/0207936 | A1 | 9/2007 | Hilliard, Jr. et al. |
| 2007/0213242 | A1 | 9/2007 | Aubrun-Sonneville |
| 2007/0213243 | A1 | 9/2007 | Yao et al. |

OTHER PUBLICATIONS

Co-pending application for: Carnali et al.; U.S. Appl. No. 12/255,365, filed Oct. 21, 2008; entitled Soap-Based Liquid Wash Formulations with Enhanced Deposition of Make-Up Agents.
Co-pending application for: Carnali et al.; U.S. Appl. No. 12/255,377, filed Oct. 21, 2008; entitled Soap-Based Liquid Wash Formulations with Enhanced Deposition of Antimicrobial Agents.
PCT International Search Report and Written Opinion on Application No. PCT/EP2009/063713 dated Oct. 28, 2011.

* cited by examiner

*Primary Examiner* — Patricia A Duffy
*Assistant Examiner* — Garen Gotfredson
(74) *Attorney, Agent, or Firm* — Ronald A. Koatz

(57) ABSTRACT

The invention relates to soap-based liquid body and facial wash compositions. Using high solvent, low water compositions and incompletely naturalized fatty acids to help structure the compositions, all in combination with modified benefit agents, enhanced deposition of conditioning and/or skin appearance and/or optical enhancing agents is achieved.

8 Claims, 2 Drawing Sheets

Figure 1. Effect of increasing levels of poly (1-vinylpyrrolidone)-graft 1-hexadecene on the stability of a titania suspension Figure 2. Surface tension of methanol / water mixtures at 20° C. Data taken from "Handbook of Chemistry and Physics, 57th Edition", R.C. Weast, Editor, CRC Press, 1976, page F-44.

SOAP-BASED LIQUID WASH FORMULATIONS WITH ENHANCED DEPOSITION OF CONDITIONING AND/OR SKIN APPEARANCE ENHANCING AGENTS

CROSS REFERENCE TO RELATED APPLICATIONS

Applicants are filing, together with this application, two related applications. One is directed to compositions for enhanced deposition of make-up agents and one to compositions for enhanced deposition of antimicrobial agents.

FIELD OF THE INVENTION

The present invention relates to soap-based liquid body and facial wash compositions. In particular, it relates to such compositions comprising conditioning and/or skin appearance enhancing (including optical enhancing) agents (e.g., optical enhancers such as titanium dioxide), and to a method of enhancing deposition of these agents. Specifically, using high solvent/low water compositions together with incompletely neutralized fatty acids (which together help structure compositions) in combination with modified benefit agents (particles and oils), enhanced deposition of the agents is achieved from unpredictably stable compositions.

BACKGROUND OF THE INVENTION

Wash-off cleanser compositions in which soap comprises 50% or more, preferably 75% or more, preferably 90% or more of the surfactant system are based on traditional fatty acid soaps (alkali metal or ammonium salts of $C_8$-$C_{24}$ fatty acids), and the soaps are beneficial for deposition of benefit agent oil which may be used in these compositions. The soap also provides "squeaky-clean" rinse preferred by many consumers.

Soap-based cleaners with high levels of benefit agents, however, can be physically unstable under storage. The benefit agents are typically dispersed as a separate phase within the formulation (e.g., as emulsion or dispersion of fine particles under about 100 microns), and may possess density higher (for most particles) or lower (for skin-enhancing oils) than the bulk phase. The high viscosity of soap-based body washes is typically due to suspension of liquid/solid crystal domains within the bulk. This phase space fills the system and helps provide creamy texture as well as to structure against phase separation.

Upon storage at high temperature, however, the crystal phase can melt to yield a lower viscosity micellar phase and the benefit agents tend to cream to the top (most oils) or sediment to the bottom (most particles). This is both esthetically unpleasing and can affect product performance (uneven dosing). The present invention circumvents the stability problem by requiring the simultaneous presence of several additives to increases the physical stability of a soap-based personal washing formulation at higher temperatures and to improve the deposition of conditioning and/or skin appearance enhancing agents.

Specifically, the invention requires 10% to 50% by weight of a fatty acid blend of $C_{12}$-$C_{18}$ fatty acids, where the degree of neutralization of the blend is between 70% and 90%. It further requires 10-40% defined co-solvents; water levels at or below 18%, preferably at or below 16%, more preferably at or below 10%; incorporation of 3-20% emollient or occlusive oil (e.g., polar oils or non-polar oils such as mineral oil or petrolatum); a skin appearance and/or optical enhancing agent (e.g., mica, talc or titanium oxide); wherein polar or non-polar oil and/or enhancing agents are modified to improve dispersibility and stability (e.g., via treatment with hydrophobic agent such as multivalent soap and/or other hydrophobic agents, such as hydrophobically modified cationic or hydrophobically modified non-ionic polymer). It is only through this unique combination of criticalities that applicants have surprisingly achieved high deposition compositions which are stable.

The following references are noted:

US 2004/0234565 A1 discloses a composition used to alter the color of skin. Pigment is dispersed in an oil phase which is in turn dispersed within an aqueous phase containing synthetic surfactant and stabilized by carboxylic acid polymers.

US 2004/0223929 A1 discusses the combination of a hydrophobically modified interference (platy) particle dispersed in a skin compatible oil which is itself emulsified within an aqueous cleansing phase containing synthetic surfactants.

US 2005/0100570 A1 claims a personal cleansing formulation consisting of an aqueous phase and a dispersed oil phase. The aqueous phase is based on anionic synthetic surfactants and displays a shear thinning rheology.

US 2006/0239953 A1 describes a rinseable personal care composition containing a dispersed moisturizing oil phase. This phase is structured by co-addition of a high modulus oil structurant such as petrolatum, microcrystalline wax, polyethylene, or polydecene.

US 2007/0207936 A1 recognizes that body washes based on rod-like or worm-like micelles with high levels of emollient oil are generally unstable towards storage at elevated temperature. Stability can be improved if the surfactant system can be formulated into a lamellar phase through the specific combination of a cationic guar gum, sodium trideceth sulfate, lauroamphoacetate, and salt. A very low shear rate must be maintained while mixing the formulation so as to keep the lamellar phase dispersed as spherulites.

U.S. Pat. No. 6,987,085 B2 describes a skin cleanser with 20-50% fatty acids and fatty acid salts with 10-30% of the fatty acids being of chain length $C_{20}$-$C_{24}$. The systems discussed are richer in fatty acids of chain length $C_{16}$ and longer than they are in acids of chain length $C_{15}$ or shorter. The degree of neutralization of the fatty acid is kept in the range 70-90% and glycols or glycol ethers are also present at levels of 5-25%. The water content of the invention can range from 20-70%.

US 2007/0213242 A1 specifies an oxyethylenated derivative of behenyl alcohol or behenic acid at a 1% level to improve the high temperature storage stability of soap-based foaming creams.

US 2007/0213243 A1 proposes to solve the poor high temperature storage stability of soap-based liquid cleansers by addition of 6-8% of an alkali-swellable, crosslinked acrylic emulsion polymer. The fatty acids and acrylic acids are first fully neutralized and then back-treated with citric acid to reduce the pH into the range 7.7-8.7, where superior storage stability is achieved.

US 2003/0078172 A1 discloses a skin cleanser which fits the category of a foaming cream—an opaque, viscous aqueous medium which is comprised of a mixture of fatty acid (soaps) or other surfactants and other additives. This invention combines a wax such as carnauba wax or beeswax (at 1-10%) and a surfactant system which forms a paracrystalline phase of direct hexagonal or cubic texture when the ambient temperature increases above 30° C. The paracrystalline phase remains stable up to at least 45° C. and so improves the storage stability of the foaming cream. The surfactants employed are a mixture of water-soluble and water-insoluble agents, such as the potassium salts of lauric and myristic acids (soluble) and the potassium salts of palmitic and stearic acid (insoluble). The insoluble salts contribute to the formation of the normal hexagonal phase. The levels of these surfactants should total 40-60%, with 5-35% insoluble and 15-35% soluble materials. Solvents such as glycerol and/or polyethylene glycol PEG 8 can be present at 5 to 20%.

Finally, as noted in cross-reference, applicants are filing on same date, in addition to the application for deposition of skin appearance and/or optical enhancing agent (e.g., $TiO_2$), one application directed to deposition of make-up agents (e.g., iron oxide) and one directed to deposition of antimicrobial agents.

BRIEF DESCRIPTION OF THE INVENTION

The present invention provides soap-based liquid compositions which are stable, even at high temperature storage, and which provide enhanced deposition of conditioning and/or appearance enhancing agents.

Specifically the invention comprises:
(1) 10-50%, preferably 25 to 40%, more preferably 30 to 40% by weight of a fatty acid blend of $C_{12}$-$C_{18}$ fatty acids;
(2) wherein degrees of neutralization of fatty acid blend is between 70% and 90%;
(3) 10-40% by weight co-solvent (e.g., selected from the group including glycerol, ethylene glycol, propylene glycol, diethylene glycol, dipropylene glycol and mixtures thereof);
(4) less than about 18%, preferably less than 16%, more preferably less than about 10% by weight water such that the ratio of co-solvent to water lies in the range 0.4 to 10, preferably 0.8 to 7, more preferably 1.0 to 5;
(5) 3 to 20% by weight emollient or occlusive oils (e.g., polar or non-polar oils such as mineral oil, petrolatum or the like);
(6) 0.01 to 15% by wt. conditioning and/or skin appearance and/or optical enhancing agents (e.g., optical particles such as mica, talc, titania or mixtures thereof); and
(7) wherein (5) and (6) are modified, for example, by treatment with hydrophobic agents such as multivalent soap and/or other hydrophobic agents such as hydrophobically modified cationic or hydrophobically modified non-ionic polymer, to improve dispersibility and stability.

The first four requirements of a high level of fatty acids, including longer chain fatty acids, which are incompletely neutralized in a low water, high polyol environment, leads to an extensive liquid/solid crystalline phase which acts to fill-space and structure the formulation. The requirements (1)-(4) raise the reversion temperature (crystalline phase-to-isotropic phase) of the crystalline phase to above that usually encountered in storage. Elevation of the reversion temperature to 35° C. or higher is preferred. Elevation to 40° C. or higher is more preferred and elevation to 45° C. or higher would be most preferred. The seventh requirement is a stabilizer for the benefiting agents (e.g., particles) or oil droplets (fifth and sixth requirements) which prevents these species from flocculating in the body/facial wash base. It is well known that the sedimentation or creaming rate of a dispersed phase increases as the second power of the dispersed particle size ("Principles of Colloid and Surface Chemistry", P. C. Hiemenz and R. Rajagopalan, Marcel Dekker, NY (1997) ISBN 0-8247-9397-8). Thus by preventing particle size growth, these undesirable processes can be delayed indefinitely. The stabilizer consists of a hydrophobic agent such as a multivalent soap and/or other hydrophobic agents such as hydrophobically modified cationic polymer, or a hydrophobically modified water-soluble polymer, all of which have an affinity for both oil droplets and benefiting particles.

The compositions can be body/facial wash liquid or foam with superior stability and deposition; or cleansing make-up with simultaneous delivery of facial cleansing and/or moisturization.

In a second embodiment, the invention relates to a method of enhancing deposition of conditioning and/or skin appearance and/or optical enhancing agents using compositions of the invention. Specifically, skin is washed (e.g., in bath, shower or any means by which liquid soap composition is typically applied) for a period of time in which composition is typically applied (e.g., from one second to up to one hour, more typically, five seconds to five to ten minutes).

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

Figure 1:
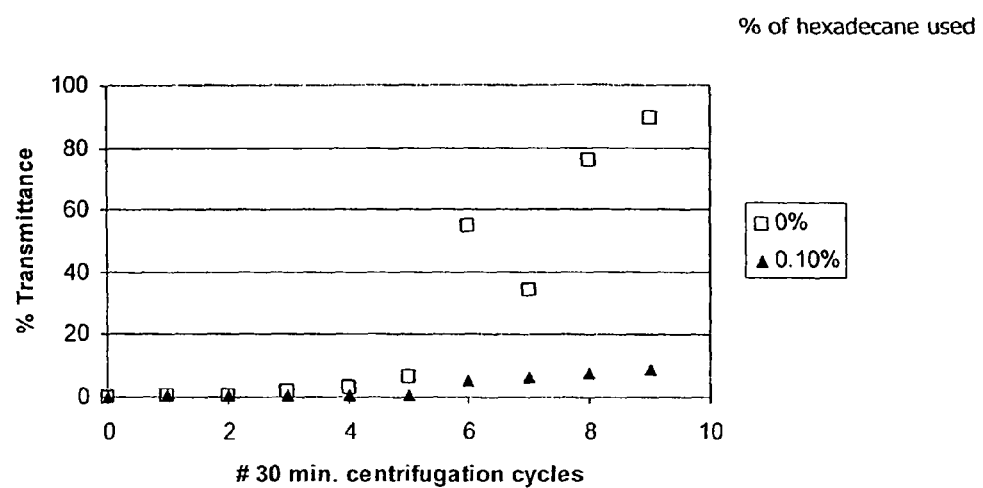
FIG. 1 shows effects of increasing levels of hydrophobically modified polymer (specifically of poly (1-vinylpyrrolidone)-graft 1-hexadecene) on particles (titania) suspension. Specifically, high levels lead to enhanced suspension/stability (as noted by less transmittance).

Many personal care or washing compositions do not provide sufficient deposition of conditioning agents, such as hydrocarbon and silicone oils, or of skin appearance enhancers, such as pigments and particles, on to skin during the cleansing process. Without such deposition, a large fraction of the benefiting agent is rinsed away during the cleansing process and therefore provides no appreciable benefit. As a result, very high levels of benefit agent may be required in the personal care composition to deliver perceivable performance—meaning increased raw materials cost and potentially hurting performance in other areas, such as lathering. One reason for this poor deposition is the detersive surfactants usually employed in personal care compositions, which work to remove oil, grease, and dirt from the skin but which also inhibit deposition of the benefit agent and remove already deposited agent. The current (partial) remedy for this problem is to use a specific surfactant system, consisting largely of synthetic anionic surfactants (detergents), combined with emulsified oil phases whose internal phase is structured with crystalline waxes and oils. This approach has been specified in several recent US Patent publications, such as US 2006/0239953 A1, US 2005/0100570 A1, and US 2007/0207936 A1.

The current invention makes use of surfactant systems which are largely devoid of synthetic surfactant (detergents), by which is meant that synthetic surfactants constitute less than 25%, preferably less than 10% of the total surfactant content of the formulation. In other words, fatty acid soaps make up 75% by weight or more of the total surfactant present. More preferably, soaps would constitute 90% or more of the total surfactant in the formulation. The total surfactant level (soaps plus other surfactants) in a typical body/facial wash is usually in the range of 15-40%. The chain length of the fatty acid soaps would typically fall into the range of $C_{12}$-$C_{18}$, with body wash formulations being richer in the shorter chain lengths within this range and facial wash formulations being richer in the longer chains.

However, soap-rich personal washing products generally show physical instability upon storage at elevated temperature and may thus be inappropriate for sale in warm weather markets. This drawback has been discussed in recent US Patent publications, with one approach being to include a long chain fatty acid soap or fatty acid derivative at levels of 1-30%. Specific additives claimed are $C_{20}$-$C_{24}$ fatty acids (U.S. Pat. No. 6,987,085 B2) and oxyethyleneated derivatives of behenyl ($C_{22}$) alcohol (US 2007/0213242 A1). The current invention requires the simultaneous presence of several additives and that the benefit agent(s) be treated with hydrophobic agent such as multivalent soap and/or other hydrophobic agents. These should be hydrophobically modified to increase the physical stability and/or dispersibility of a soap-based personal washing formulation at higher temperatures and to improve the deposition of conditioning or skin appearance enhancing agents.

More specifically the invention comprises:
(1) 10-50% by weight of a fatty acid blend of $C_{12}$-$C_{18}$ fatty acids; Preferably, the level of fatty acid blend will be 20% to 40%, more preferably 30% to 40%.
(2) wherein degrees of neutralization of fatty acid blend is between 70% and 90%; preferably between 75% and 85%, most preferably between 77% and 81%.
(3) 10-40% by weight co-solvent (e.g., selected from the group including glycerol, ethylene glycol, propylene glycol, diethylene glycol, dipropylene glycol and mixtures thereof);
(4) less than about 18%, preferably less than 16%, more preferably less than about 10% by weight water, such that the ratio of cosolvent to water lies in the range 0.4 to 10, preferably 0.8-7, more preferably 1.0 to 5.
(5) 3 to 20% by weight oils or emollients (e.g., polar or non-polar oils such as mineral oil or petrolatum);
(6) 0.01 to 15%, preferably 1 to 10% by wt. conditioning and/or skin appearance and/or optical enhancing particles (e.g., optical particles such as mica, talc or titania or mixtures thereof);
(7) wherein (5) and (6) are modified, for example, by treatment with hydrophobic agent such as multivalent soap and/or other hydrophobic agents such as hydrophobically modified cationic or hydrophobically modified non-ionic polymer, to improve dispersibility and stability.

As described in Example 32 below, hydrophobically modified particles of the invention are those which show a critical surface tension (measured by flotation test protocol described) of 40 milli-Newtons per meter (mN/m) or below, preferably 30 mN/m or below. Particles of the invention all meet this criterion.

As far as hydrophobic modifying agents, typically soaps and other non-polymeric agents would have hydrophile-lipophilic balance (HLB) number of 1 to 5. Typically, such agents are either completely non-dispersible or poorly dispersible in water. This is described, for example, in "Nonionic Surfactants" by Paul Becher, edited by M. J. Schick, Marcel Dekker, Inc., NY (1966), hereby incorporated by reference into the subject application. Hydrophobically modified cationic or nonionic polymers are polymers containing hydrophobic co-monomers. Hydrophobicity is a relative property (see US 2006/0266488 A1), but is preferably embodied by co-monomers having at least 6 or more carbons, preferably 8 or more carbons.

The invention comprises 10-50%, preferably 20-40%, more preferably 30-40% by wt. of blend of $C_{12}$ to $C_{18}$ fatty acids. A typical blend may comprise a mix of lauric, myristic, palmitic and stearic acids.

The composition may comprise a small amount of synthetic anionic (e.g., taurate, sulfates) and/or nonionic surfactants although, if needed, these will typically comprise less than 5%, preferably 0.5-4% of the composition.

The degree of neutralization of the fatty acids noted above (fatty acid blend) is between 70 and 90%, preferably between 75 and 85%, more preferably 77 to 81%. Combination of underneutralized fatty acids in low water, high co-solvent system are believed to help produce liquid/solid crystalline phase needed to space-fill and structure.

As indicated, 10-40% co-solvent is used. Preferred co-solvent (to produce the right environment) includes glycerol, ethylene glycol, propylene glycol, diethylene glycol, dipropylene glycol and mixtures thereof.

Particularly preferred co-solvents are propylene and dipropylene glycol as well as diethylene glycol. If dipropylene glycol, propylene glycol or diethylene glycol are used, it is preferred that alone or in combination they comprise >30%, preferably >40%, more preferably >50% of the co-solvent system as these offer particularly unpredictable improvements.

As also indicated, low water environment (18% by weight or less, preferably 16% by weight or less, more preferably 10% by weight or less) is also needed to help get the right liquid/crystal crystalline phase.

Another unpredictable aspect of the invention in this regard is the ratio of co-solvent to water. As this ratio increases (higher co-solvent, lower water), deposition is particularly enhanced. Ratios of 0.4 to 10, preferably 0.8 to 7, more preferably 1 to 5 are preferred.

The formulation also requires 3 to 20% oils and/or emollients (e.g., mineral oil, petrolatum). The oil can belong to the class of occlusive oils, which are defined as oils that are liquid or semisolid at the storage and/or application temperature and which are safe for use in cosmetics, being either beneficial or inert to skin. The example of compatible oils for the present invention includes polar and non-polar oils such as hydrocarbon oils, silicone oils, ester oils or mixtures thereof. Some of the oils are thickened to enhance the rheological properties of the occlusive oils and the products. Two preferred oils included mineral oil and petrolatum. In general, the oil can be modified by addition of a stabilizer—a hydrophobically modified water-soluble polymer with affinity for oil droplets and benefiting agents. One preferred polymer is poly(1-vinylpyrrolidone)-graft 1-hexadecene (e.g., from Sigma Aldrich Inc.).

The formulation also requires 0.01 to 15%, preferably 0.2 to 10% by wt. of a skin appearance and/or optical enhancing agent. The agent is preferably an optical particle such as mica, talc or titania ($TiO_2$). The surface properties of the particles or pigments used in the present invention should be naturally hydrophobic or hydrophobically modified. Surface modification is performed to alter the physical properties and can include lipophilic treatments with amino silicone to simplify the dispersion of pigments in anhydrous systems, hydrophobic treatments with silanes and methicone to maximize water repellency, perfluoroalkyl phosphate treatments to make the treated pigment both lipophobic and hydrophobic and by hydrophobic modification via treatment with multivalent soaps or with polymers/co-polymers, such as modification with aluminum soap of myristic, palmitic, stearic acid, etc. or with methicone, silica, acrylate, silicon co polymer, carnauba wax, polyethylene, etc. In short the invention is intended to include all hydrophobically modified particles surface treated by surface treatment houses including those by Kobo products, US cosmetics, Roana EMD, Cardre, etc. Hydrophobicity can be tested as described in the invention.

In another co-pending application, the compositions are used for deposition of make-up agents (e.g., metal oxide pigments).

As noted, the range of conditioning and/or skin and/or optical enhancing agents may be 0.01 to 15%, preferably 1-10% by wt. of the composition.

The requirements (1)-(4) help raise temperatures at which crystalline phase reverts to isotopic (crystalline being more stable than isotropic) so that the composition is more stable at elevated temperatures. Reversion at temperatures of 35° C. or up, preferably 40° C. and more preferably 45° C. and up is preferred.

The following examples are intended to further illustrate the invention and are not intended to limit the invention in any way.

Protocols

Deposition Test Protocol—The following test was found to give reproducible results for pigment deposition under controlled conditions:

0.2 g of neat formulation was diluted with 3 mL of hot tap water (50° C.) in a 1 ounce cup and dispersed well by treating for 20 seconds with an ultrasonic processor (Sonics Vibra Cell) at an output power of 20 watts. A 3×6 $cm^2$ piece of Parafilm was placed, smooth side up, on a flat countertop and one-half of the surface was covered with adhesive tape, leaving a 3×3 $cm^2$ surface exposed. 0.3 g of the resulting wash liquor was delivered via a pipette to the center of the Parafilm and the liquor was lightly rubbed in (0.2 lb/$in^2$) using a gloved fore-finger for 30 s. The treated area should be centered on the edge of the taped-off region. The Parafilm was rinsed under a steady stream of warm water (40° C., flow rate of 100 cc/second) for 10 seconds and patted dry. Upon careful removal of the adhesive tape, a sharp interface was created between the treated and untreated Parafilm. The volume of hot water used to form the wash liquor can be varied over a wide range (for example 1-10 mL), but 3 mL was chosen to maximize discrimination of the tested formulations.

The Parafilm sheet was next mounted on a Nikon Eclipse E600 Light Microscope and a brightfield image of the treated area was captured at 100× magnification using a Nikon Digital Camera DXM1200. The imaged area should include the interface between the treated and control Parafilm surfaces. An open-source image analysis software package (Image J) was used to convert the photo-micrograph to grey scale and thresholding was performed to distinguish the deposited particles. Image J is freely available from the web site: rsb.info.nih.gov/ij. The average pixel grey scale was determined on the untreated half of the image and used to correct that of the treated half. Several images were taken from different parts of each piece of treated Parafilm and several treated pieces were made up for each formulation. The pixel averages and error bars for each formulation were obtained from averaging 8 to 10 images. A percentage of surface coverage was then calculated by dividing the pixel average by 255 (equivalent to complete coverage) and then multiplying by 100.

Figure 2:
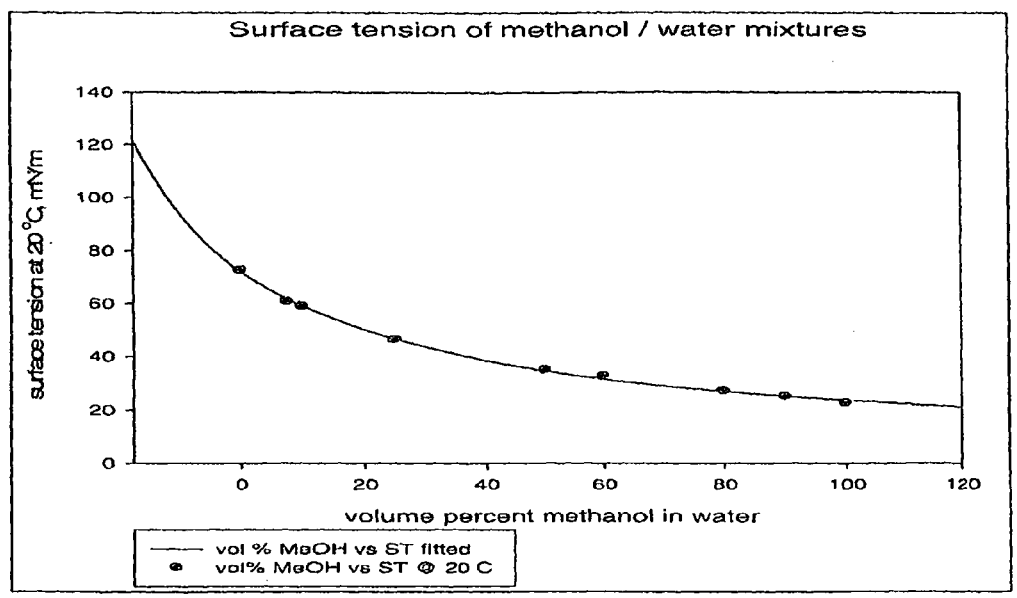
FIG. 2 is surface tension of methanol/water mixtures at 20° C. used in the description of the flotation test protocol. Data is taken from "Handbook of Chemistry and Physics, $57^{th}$ Edition", R. C. West, Editor, CRC Press, 1976, page F-44.

Flotation Test Protocol—To gauge the degree of hydrophobic modification of enhancing particles, the surface energy of the isolated particles was estimated by measuring the critical surface tension for flotation, as described by M. C. Williams and D. W. Fuerstenau ("A simple flotation method for rapidly assessing the hydrophobicity of coal particles", International Journal of Mineral Processing, volume 20, pages 153-157 (1987)). In this measurement, a monolayer of closely sized particles is carefully deposited on the surface of a methanol/water mixture. The particles generally either float on the surface or are immediately imbibed by the liquid and sink. The ratio of methanol to water is varied and, as a result, the surface tension of the solution varies as shown in FIG. 2 (data from "Handbook of Chemistry and Physics, $57^{th}$ Edition", R. C. Weast, Editor, CRC Press, 1976, page F-44). The approximate fraction of the particles which float (determined visually) can be plotted versus the surface tension corresponding to the appropriate methanol/water mixture. The particles which float are hydrophobic for a given surface tension, while those which sink are hydrophilic. The surface tension, at which 50% of the particles sink/float was taken as the critical surface tension for flotation. By analogy with the better known critical surface tension for wetting (A. W. Adamson, "Physical Chemistry of Surfaces, $3^{rd}$ Edition", Wiley, 1976), this critical surface tension for flotation is taken as an estimate for the particle surface energy. The reasoning is that the liquid will not wet the particle (causing it to sink) unless its surface tension is less than the surface energy of the particle. Thus the lower the critical surface tension for wetting, the more hydrophobic is the particle. In practice, hydrophobically modified particles were found to have critical surface tensions of 40 mN/m or below, more preferably 30 mN/m and below. This test was used to show that treated particles of the invention did become hydrophobically modified.

EXAMPLES

Example 1

This example demonstrates the stabilization of $TiO_2$ in mineral oil using a hydrophobically modified water-soluble polymer. The polymer is a sample of poly (1-vinylpyrrolidone)-graft 1-hexadecene purchased from Sigma-Aldrich Inc. This polymer is soluble at a level of greater than 10% in mineral oil (White Paraffin Oil, 180-190 Saybolt Viscostiy). A 1% polymer-in-mineral oil solution was prepared and used to make further dilutions to 0.5%, 0.2%, 0.1%, 0.05%. 0.02%, and 0.01% in mineral oil. A 2% dispersion of aluminum myristate coated $TiO_2$ in mineral oil was prepared in parallel using an ultrasonic probe (Ultrasonic Processor from Sonics Vibra-Cell). Then, 0.2 g of this dispersion was diluted to 5 g with one of the polymer-containing mineral oil solutions and thoroughly sonicated using three, ten second pulses at a power setting of 80%. A 3 mL portion of each sample was transferred to a cylindrical cuvette and the initial transmittance at 450 nm of the sample was measured using a Cary 330 Bio/UV Spectrophotometer. Following this measurement, each cuvette was centrifuged for 30 minutes at 1000 rpm (180 rcf) on an Eppendorf 5804 Centrifuge. The cuvette transmittance was then remeasured and the sample subjected to a second 30 minute treatment in the centrifuge. This sequential process was repeated and the trend of measured transmittance with centrifugation cycles is shown in FIG. 1.

As seen, at levels as low as 0.10% polymer, transmittance value remained low even after high number of centrifugation cycles. This indicates the $TiO_2$ remained in suspension. Separate experiments indicate this polymer gives some benefit under these conditions down to polymer levels as low as 0.01%.

Formulation Examples 2-4

Effect of Dipropylene Glycol (DPG) to Water Ratio On Deposition, Comparative Examples A and B In examples below, the co-solvent level of facial foam formulation is increased sequentially and the water level reduced in proportion.

| Full chemical name | A | Ex. 2 | B | Ex. 3 | Ex. 4 |
|---|---|---|---|---|---|
| Lauric acid (fatty acid) | 4.90 | 4.90 | 4.90 | 4.90 | 4.90 |
| Myristic acid (fatty acid) | 8.05 | 8.05 | 8.05 | 8.05 | 8.05 |
| Palmitic acid (fatty acid) | 10.69 | 10.69 | 10.69 | 10.69 | 10.69 |
| Stearic acid (fatty acid) | 9.37 | 9.37 | 9.37 | 9.37 | 9.37 |
| Potassium hydroxide | 5.84 | 5.84 | 5.84 | 5.84 | 5.84 |
| Sodium N-cocoyl N-methyl Taurate (surfactant) | 2.19 | 2.19 | 2.19 | 2.19 | 2.19 |
| Polyoxyethylene cetylether (20 E.O)/ Brij-58 (surfactant) | 0.00 | 0.00 | 0.00 | 0.00 | 0.00 |
| Dipropylene Glycol (cosolvent) | 8.80 | 20.00 | 0.00 | 17.00 | 13.80 |
| Glycerin (cosolvent) | 11.80 | 11.80 | 11.80 | 11.80 | 11.80 |
| Maltitol solu. | 3.00 | 3.00 | 3.00 | 3.00 | 3.00 |
| Aluminum dimyristate coated $TiO_2$ | 4.00 | 4.00 | 4.00 | 4.00 | 4.00 |
| Merquat-100 (cationic polymer) | 0.40 | 0.40 | 0.40 | 0.40 | 0.40 |
| Mineral oil (oil) | 2.00 | 2.00 | 2.00 | 2.00 | 2.00 |
| Petroleum Jelly (PJ) (oil) | 8.00 | 8.00 | 8.00 | 8.00 | 8.00 |
| Water to 100 | 20.96 | 9.76 | 29.76 | 12.76 | 15.96 |

The above examples demonstrate the utility of high levels of cosolvent and simultaneous low water levels in improving deposition of particle, e.g. $TiO_2$. The examples show that, when dipropylene glycol (DPG) is one of the solvents in the cosolvent system, deposition is even better. Indeed, the greater the ratio of DPG/water, the better the deposition. This is seen from deposition results below:

| Example No. | Cosolvent/water ratio | Percent surface coverage |
|---|---|---|
| Comparative B (0% DPG) | 0.4 | 5.7 ± 1 |
| Comparative A (8.8% DPG) | 0.98 | 19.8 ± 8 |
| 4 (13.8% DPG) | 1.6 | 38.4 ± 15 |
| 3 (17% DPG) | 2.3 | 37.5 ± 15 |
| 2 (20% DPG) | 3.3 | 74.6 ± 16 |

The above examples demonstrate the utility of high levels of cosolvent and simultaneous low water levels in improving deposition of titania particle.

Formulation Example 5-9

Degree of Soap Neutralization

| | Degree of Neutralization | | | | |
|---|---|---|---|---|---|
| | 75.0% | 77.5% | 80.0% | 82.5% | 85.0% |
| Full chemical name | Ex. 5 | Ex. 6 | Ex. 7 | Ex. 8 | Ex. 9 |
| Lauric acid | 4.90 | 4.90 | 4.90 | 4.90 | 4.90 |
| Myristic acid | 8.05 | 8.05 | 8.05 | 8.05 | 8.05 |
| Palmitic acid | 10.69 | 10.69 | 10.69 | 10.69 | 10.69 |
| Stearic acid | 9.37 | 9.37 | 9.37 | 9.37 | 9.37 |
| Potassium hydroxide | 5.64 | 5.84 | 6.02 | 6.22 | 6.40 |
| Sodium N-cocoyl N-methyl Taurate | 2.19 | 2.19 | 2.19 | 2.19 | 2.19 |
| Polyoxyethylene cetylether (20 E.O)/ Brij-58 | 0.00 | 0.00 | 0.00 | 0.00 | 0.00 |
| Dipropylene Glycol (Co-solvent) | 13.80 | 13.80 | 13.80 | 13.80 | 13.80 |
| Glycerin | 11.80 | 11.80 | 11.80 | 11.80 | 11.80 |
| Maltitol solu. | 3.00 | 3.00 | 3.00 | 3.00 | 3.00 |
| $TiO_2$ (particle) | 4.00 | 4.00 | 4.00 | 4.00 | 4.00 |
| Merquat-100 (cationic) | 0.40 | 0.40 | 0.40 | 0.40 | 0.40 |
| Mineral oil (oil) | 2.00 | 2.00 | 2.00 | 2.00 | 2.00 |
| PJ (oil) | 8.00 | 8.00 | 8.00 | 8.00 | 8.00 |
| Water to 100 | 15.76 | 15.96 | 15.78 | 15.58 | 15.40 |

The above examples demonstrate the utility of controlling the degree of fatty acid neutralization to lie between 70% and 90%, especially 77 and 81% in maintaining formulation physical stability and optimal deposition.

More specifically, as seen from the Table below, in the optimum range between 77 and 81% neutralization, the greatest deposition is achieved as seen from percent surface coverage results.

| Ex. | Degree of Neutralization | Percent Surface Coverage |
|---|---|---|
| 5 | 75% neutralization | 26 ± 10 |
| 6 | 77.5% neutralization | 38.4 ± 15 |
| 7 | 80.0% neutralization | 38.8 ± 15 |
| 8 | 82.5% neutralization | 2 ± 2 |
| 9 | 85% neutralization | 16 ± 8 |

Examples 10-14

| Full chemical name | 10 | 11 | 12 | 13 | 14 |
|---|---|---|---|---|---|
| Lauric acid | 4.90 | 4.90 | 4.90 | 4.90 | 4.90 |
| Myristic acid | 8.05 | 8.05 | 8.05 | 8.05 | 8.05 |
| Palmitic acid | 10.69 | 10.69 | 10.69 | 10.69 | 10.69 |
| Stearic acid | 9.37 | 9.37 | 9.37 | 9.37 | 9.37 |
| Potassium hydroxide | 5.64 | 5.84 | 6.02 | 6.22 | 6.40 |
| Sodium N-cocoyl N-methyl Taurate | 2.19 | 2.19 | 2.19 | 2.19 | 2.19 |
| Polyoxyethylene cetylether (20 E.O)/ Brij-58 | 0.00 | 0.00 | 0.00 | 0.00 | 0.00 |
| Dipropylene Glycol | 20.00 | 20.00 | 20.00 | 20.00 | 20.00 |
| Glycerin | 11.80 | 11.80 | 11.80 | 11.80 | 11.80 |
| Maltitol solu. | 3.00 | 3.00 | 3.00 | 3.00 | 3.00 |

-continued

| Full chemical name | 10 | 11 | 12 | 13 | 14 |
|---|---|---|---|---|---|
| $TiO_2$ | 4.00 | 4.00 | 4.00 | 4.00 | 4.00 |
| Merquat-100 | 0.40 | 0.40 | 0.40 | 0.40 | 0.40 |
| Mineral oil | 2.00 | 2.00 | 2.00 | 2.00 | 2.00 |
| Petroleum Jelly | 8.00 | 8.00 | 8.00 | 8.00 | 8.00 |
| Water to 100 | 9.96 | 9.76 | 9.58 | 9.38 | 9.20 |

The above examples are analgous to examples 5-9, but using 20% DPG, instead of 13.8. Again, they demonstrate the utility of controlling the degree of neutralization between 70% and 90%.

Specifically, as seen from the Table below, in the optimum range of between 77 and 81% neutralization, the greatest deposition is achieved as seen again by percent surface coverage.

| Example | Degree of Neutralization | Percent surface coverage |
|---|---|---|
| 10 | 75% neutralization | 24 ± 12 |
| 11 | 77.5% neutralization | 60 ± 16 |
| 12 | 80.0% neutralization | 52 ± 20 |
| 13 | 82.5% neutralization | 37 ± 16 |
| 14 | 85% neutralization | 43 ± 16 |

Formulation Examples 15-27

Best Co-Solvents

Variations are made on the general formulation given in the table below by varying the type of co-solvent, keeping the co-solvent level fixed at 20%, on top of a baseline glycerin level of 11.8%, and the degree of soap neutralization at 77.5%.

| Full chemical name | Base for Example |
|---|---|
| Lauric acid | 4.90 |
| Myristic acid | 8.05 |
| Palmitic acid | 10.69 |
| Stearic acid | 9.37 |
| Potassium hydroxide | 5.84 |
| Sodium N-cocoyl N-methyl Taurate | 2.19 |
| Polyoxyethylene cetylether (20 E.O)/Brij-58 | 0.00 |
| Cosolvent | 20.00 |
| Glycerin | 11.80 |
| Maltitol solu. | 3.00 |
| $TiO_2$ | 4.00 |
| Merquat-100 (cationic polymer) | 0.40 |
| Mineral oil | 2.00 |
| Petroleum Jelly | 8.00 |
| Water to 100 | 9.76 |

The results of deposition studies made with each formulation are as follow:

| Example No. | Cosolvent (solubility parameter*, $\sqrt{(cal/cm^3)}$) | Percent surface coverage |
|---|---|---|
| 15 | Ethylene glycol (14.6) | 13 ± 8 |
| 16 | Diethylene glycol (12.1) | 29 ± 12 |
| 17 | PEG 200 (12.8) | 21 ± 12 |
| 18 | PEG 400 (11.1) | 12 ± 6 |
| 19 | Propylene glycol (12.6) | 35 ± 8 |
| 20 | Dipropylene glycol (10.0) | 60 ± 16 |
| 21 | PPG 9 (7.5) | 10 ± 4 |
| 22 | Butylene glycol (12.8) | 18 ± 8 |
| 23 | Dipropylene glycol methyl ether (9.3) | 5 ± 1 |
| 24 | Glycerin (16.5) | 6 ± 2 |
| 25 | Sorbitol (18.7) | 7 ± 4 |
| 26 | Urea (18.8) | 14 ± 8 |
| 27 | Sucrose | 4 ± 2 |

*values from: "Polymer Handbook", Eds. Brandrup, J.; Immergut, E. H.; Grulke, E. A., 4$^{th}$ Edition, John Wiley, New York, 1999, and Richardson, J. C.; Dettmar, P. W.; Hampson, F. C.; Melia, C. D. European J. Pharmaceutical Sci. 23, 49-56 (2004).

The most preferred cosolvents for body/facial washes are polyhydric alcohols (see US 2007/0293411A1, US 2008/0008672 A1) such as glycerol, polyethylene glycol (PEG), propylene glycol, polypropylene glycol (PPG), butylene glycol, and sorbitol. These cosolvents are compared above with dipropylene glycol and the results demonstrate the superiority of dipropylene glycol over other typical glycols and glycol ethers for improving deposition from soap-rich formulations.

Noting the chemical structures of some of the cosolvents examined:
Ethylene glycol: $HOCH_2CH_2OH$
Diethylene glycol: $HOCH_2CH_2$—O—$CH_2CH_2OH$
PEG 200 (3): $H(OCH_2CH_2)_3OH$
PEG 400 (8): $H(OCH_2CH_2)_8OH$
Propylene glycol: $HOCH(CH_3)$—$CH_2OH$
Dipropylene glycol: $HOCH(CH_3)$—$CH_2$—O—$CH_2$—$(CH_3)CHOH$
PPG 9: $H(OCH(CH_3)$—$CH_2)_9OH$
Butylene glycol: $HOCH(CH_3)CH_2CH_2OH$ A trend can be observed in which, over the homologous series ethylene, propylene, and butylene, deposition shows a maximum at propylene. Further, as a function of the degree of polymerization, a maximum is found at two repeat units. Dipropylene glycol represents the optimum of both these trends. It can also be observed in the above table that there is no simple correlation of deposition with the Hildebrand Solubility Parameter.

Comparative Examples C-F

Other Controls

In these examples, we demonstrate that certain aspects of the invention are critical for the claimed functions. Identical formulations are prepared at 77.5% soap neutralization and 20% dipropylene glycol, but with one or more critical ingredients withheld.

| Full chemical name | C | D | E | F |
|---|---|---|---|---|
| Lauric acid | 4.90 | 4.90 | 4.90 | 4.90 |
| Myristic acid | 8.05 | 8.05 | 8.05 | 8.05 |
| Palmitic acid | 10.69 | 10.69 | 10.69 | 10.69 |
| Stearic acid | 9.37 | 9.37 | 9.37 | 9.37 |
| Potassium hydroxide | 5.84 | 5.84 | 5.84 | 5.84 |
| Sodium N-cocoyl N-methyl Taurate | 2.19 | 2.19 | 2.19 | 2.19 |
| Polyoxyethylene cetylether (20 E.O)/Brij-58 | 0.00 | 0.00 | 0.00 | 0.00 |
| Dipropylene Glycol | 20.00 | 20.00 | 20.00 | 20.00 |
| Glycerin | 11.80 | 11.80 | 11.80 | 11.80 |
| Maltitol solu. | 3.00 | 3.00 | 3.00 | 3.00 |
| $^1$Aluminum dimyristate coated $TiO_2$ | 4.00 | 4.00 | 4.00 | 0.00 |
| $^2$Standard anatase titanium dioxide | 0.00 | 0.00 | 0.00 | 4.00 |

-continued

| Full chemical name | C | D | E | F |
|---|---|---|---|---|
| Merquat-100 | 0.40 | 0.00 | 0.00 | 0.40 |
| Mineral oil | 0.00 | 2.00 | 0.00 | 2.00 |
| Petroleum Jelly | 0.00 | 8.00 | 0.00 | 8.00 |
| Water to 100 | 19.76 | 10.16 | 20.16 | 9.76 |

[1]US Cosmetics Corporation MT-TAK-77891.
[2]American International Chemical, Inc. TIOKFP.

The results of deposition studies made with each formulation are as follow:

| Example No. | Percent surface coverage |
|---|---|
| C (no oil) | 1 ± 1 |
| D (no polymer) | 41 ± 12 |
| E (no oil or polymer) | 1 ± 1 |
| F (uncoated pigment) | 1 ± 1 |

These results clearly demonstrate the criticality of the oil component and the hydrophobic modification of the pigment in achieving effective levels of deposition. The example which was different from the invention only in the absence of cationic polymer (D) showed good deposition, but had poor physical storage stability, phase separating after one week's storage at 45° C. Example F had oil, cationic and particle but, because particle was not coated, deposition was very low.

Formulation Examples 28-31

Other Hydrophobically Coated Pigments

In these examples, we demonstrate that hydrophobically modified pigments other than titanium may be incorporated into the invention and can be shown to be deposited during a simulated wash. These findings support the invention of a cleansing make-up. The degree of soap neutralization is held at 77.5% and all formulations contain 20% dipropylene glycol.

| Full chemical name | 28 | 29 | 30 | 31 |
|---|---|---|---|---|
| Lauric acid | 4.90 | 4.90 | 4.90 | 4.90 |
| Myristic acid | 8.05 | 8.05 | 8.05 | 8.05 |
| Palmitic acid | 10.69 | 10.69 | 10.69 | 10.69 |
| Stearic acid | 9.37 | 9.37 | 9.37 | 9.37 |
| Potassium hydroxide | 5.84 | 5.84 | 5.84 | 5.84 |
| Sodium N-cocoyl N-methyl Taurate | 2.19 | 2.19 | 2.19 | 2.19 |
| Polyoxyethylene cetylether (20 E.O)/Brij-58 | 0.00 | 0.00 | 0.00 | 0.00 |
| Dipropylene Glycol | 20.00 | 20.00 | 20.00 | 20.00 |
| Glycerin | 11.80 | 11.80 | 11.80 | 11.80 |
| Maltitol solu. | 3.00 | 3.00 | 3.00 | 3.00 |
| [1]Aluminum dimyristate coated $TiO_2$ | 4.00 | 2.67 | 2.00 | 2.00 |
| [2]Red iron oxide | 0.00 | 1.33 | 0.00 | 1.33 |
| [3]Yellow iron oxide | 0.00 | 0.00 | 2.00 | 0.67 |
| Merquat-100 | 0.40 | 0.40 | 0.40 | 0.40 |
| Mineral oil | 2.00 | 2.00 | 2.00 | 2.00 |
| Petroleum Jelly | 8.00 | 8.00 | 8.00 | 8.00 |
| Water to 100 | 9.76 | 9.76 | 9.76 | 9.76 |

[1]US Cosmetics Corporation MT-TAK-77891.
[2]Kobo BERO/MM3 INCI CI 77491 coated with magnesium dimyristate.
[3]Kobo BGYO-BAS2 INCI CI 77492 coated with triethyoxysilylethyl polydimethylsiloxyethyl hexyl dimethicone.

| Example No. | $\Delta L^*$ | $\Delta a^*$ | $\Delta b^*$ |
|---|---|---|---|
| 28, coated titanium dioxide | 43.87 | −1.90 | −7.10 |
| 29, coated $TiO_2$ and red iron oxide | 44.27 | 5.02 | 1.29 |
| 30, coated $TiO_2$ and yellow iron oxide | 48.36 | −1.67 | 7.14 |
| 31, coated $TiO_2$ and red and yellow iron oxides | 41.41 | 10.21 | 8.46 |

These formulations were used to create wash liquors which were then used to treat sheets of Parafilm substrate, as in the Deposition Test Protocol. Then L*a*b* measurements were made on the sheets using a HunterLab LabScan XE instrument. The L*a*b* color space has dimension L* for luminance and a* and b* for color-opponent dimensions. In this context, the L* component closely matches the human perception of lightness, with L*=0 corresponding to black and L*=100 to white. The dimension a* indicates the position of a color between green and red, with negative a* indicating green and positive values indicating red. Similarly, the dimension b* indicates the position between blue (negative value of b*) and yellow (positive value). Pieces of parafilm substrate were measured prior to any treatment to establish base L*a*b* values. After the simulated wash with a wash liquor derived from one of the above example formulations, the measurement was repeated and the differences in each of the color space dimensions, $\Delta L^*$, $\Delta a^*$, and $\Delta b^*$ were determined as presented above. The data shown are the average of at least 6 determinations. Relative to the titania pigment, addition of the red iron oxide gives a distinct increase in the red component ($\Delta a^*$) and in the yellow component ($\Delta b^*$). Addition of the yellow iron oxide gives a significant increase in the yellow color component ($\Delta b^*$) and addition of both iron oxides strongly increases both the red and yellow color components. These results show that the iron oxide pigments are being deposited on the substrate and giving their characteristic colors.

Additionally, other types of particles could be included in this invention, specifically high void fraction or porous particles which could be loaded with perfume, antimicrobial actives, sunscreen actives, or pigments. The only requirement is that these particles be hydrophobically modified.

Example 32

Hydrophobic Modification of Enhancing Particle to Improve Its Dispersibility and Stability The Flotation Test is used to gauge the degree of hydrophobic modification of enhancing particles. The critical surface tension for flotation was measured as described in the protocol and the fraction of a given type of particles floating in a methanol/water mixture with a surface tension of 40 or 30 mN/m is indicated. Particles which still float at a surface tension of 40 mM/m or lower are deemed hydrophobic, those floating at a surface tension of 30 mN/m or lower are deemed very hydrophobic.

| Example | % floated at 40 mN/m | % floated at 30 mN/m |
|---|---|---|
| [1]Standard titanium dioxide | 0 | 0 |
| [2]Coated titanium dioxide | 100 | 100 |

-continued

| Example | % floated at 40 mN/m | % floated at 30 mN/m |
|---|---|---|
| [3]Red iron oxide | 100 | 100 |
| [4]Yellow iron oxide | 100 | 100 |

[1]American International Chemical, Inc. TIOKFP.
[2]US Cosmetics Corporation MT-TAK-77891 coated with aluminum dimyristate.
[3]Kobo BERO/MM3 INCI CI 77491 coated with magnesium dimyristate.
[4]Kobo BGYO-BAS2 INCI CI 77492 coated with triethyoxysilylethyl polydimethylsiloxyethyl hexyl dimethicone.

The results of this test demonstrate that the treated particles under consideration are very hydrophobic.

Examples 33

Effect of Soap Level on Storage Stability

A series of formulations were prepared at a fixed degree of fatty acid neutralization of 77.5% but with declining levels of total soap: 33, 30, 27.5, 25, 22.5, 20, 17.5, and 15%. The systems were left undisturbed in a storage room, thermostated at 45° C., for twelve weeks. All samples with total soap levels below 30% split into a water-rich phase and a soap-rich phase during storage, showing that a minimal soap level is a necessary requirement for a viable product.

The invention claimed is:

1. A liquid soap composition comprising:
   (a) 25-50% by weight of a fatty acid blend consisting essentially of $C_{12}$-$C_{18}$ fatty acids;
   (b) wherein degrees of neutralization of fatty acid blend is between 70% and 90%;
   (c) 10-40% by weight of a co-solvent system;
   (d) less than about 18% by weight water;
   (e) 3 to 20% by weight emollient or occlusive oil;
   (f) 0.01 to 15% by wt. skin appearance and/or optical enhancing agent; and
   (g) wherein (e) and (f) are modified by treatment with multivalent soap and/or hydrophobic agent selected from the group consisting of hydrophobically modified cationic polymer, hydrophobically modified non-ionic polymer and mixtures thereof;
   wherein ratio of co-solvent (c) to water (d) is from 0.56 to 10
   wherein said cosolvent system comprises (i) dipropylene glycol, and (ii) glycerol; wherein said dipropylene glycol comprises >30% of the cosolvent system.

2. A composition according to claim 1 wherein oil is a polar or non-polar oil selected from the group consisting of hydrocarbon oils, silica oils, ester oils and mixtures thereof.

3. A composition according to claim 1 wherein oil is mineral oil or petrolatum.

4. A composition according to claim 1 wherein said optical enhancing agents are optical enhancing particles.

5. A composition according to claim 4 wherein said particles are selected from the group consisting of mica, talc, titania and mixtures thereof.

6. A composition according to claim 1 comprising 30 to 40% by weight fatty acid.

7. A composition according to claim 1 wherein degree of neutralization is between 75% and 85%.

8. A method of enhancing deposition of skin appearance enhancing agents which method comprises washing skin with liquid soap composition comprising:
   (a) 10-50% by weight of a fatty acid blend consisting essentially of $C_{12}$-$C_{18}$ fatty acids;
   (b) wherein degrees of neutralization of fatty acid blend is between 70% and 90%;
   (c) 10-40% by weight of a co-solvent system;
   (d) less than about 18% by weight water;
   (e) 3 to 20% by weight non emollient or occlusive oil;
   (f) 0.01 to 15% by wt. skin appearance and/or optical enhancing agent; and
   (g) wherein (e) and (f) are modified by treatment with multivalent soap and/or hydrophobic agent selected from the group consisting of hydrophobically modified cationic polymer, hydrophobically modified non-ionic polymer and mixtures thereof;
   wherein ratio of co-solvent in (c) to water (d) is from 0.56 to 10;
   wherein said cosolvent system comprises (i) dipropylene glycol, and (ii) glycerol; wherein said dipropylene glycol comprises >30% of the cosolvent system.

* * * * *